United States Patent [19]

Stone

[11] Patent Number: 5,620,604
[45] Date of Patent: Apr. 15, 1997

[54] DIALYSIS SYSTEM AND METHOD FOR REMOVING TOXIC MATTER FROM THE SERUM OF THE LARGE INTESTINE

[76] Inventor: Andrew Stone, 5818 NW 34th Way, Boca Raton, Fla. 33496

[21] Appl. No.: 225,894

[22] Filed: Apr. 11, 1994

Related U.S. Application Data

[63] Continuation-in-part of Ser. No. 922,673, Jul. 30, 1992, abandoned.

[51] Int. Cl.$^6$ .......................... A61M 1/00; A61M 1/28; A61M 5/00; A61M 25/10
[52] U.S. Cl. .................. 210/645; 210/90; 210/97; 210/104; 210/121; 210/143; 210/257.1; 210/258; 210/739; 210/741; 210/744; 210/748; 210/808; 604/28; 604/29; 604/30; 604/31; 604/51; 604/65; 604/67; 604/96; 604/101; 604/102; 604/259; 604/260
[58] Field of Search .................. 210/90, 97, 104, 210/111, 121, 143, 257.1, 748, 258, 739, 646, 650, 741, 744, 746, 808, 929, 645; 604/28, 29, 30, 31, 51, 65, 67, 81, 96, 173, 259, 260, 97, 101, 102; 607/133

[56] References Cited

U.S. PATENT DOCUMENTS

| | | | |
|---|---|---|---|
| 4,190,047 | 2/1980 | Jacobsen et al. | 210/929 |
| 4,252,115 | 2/1981 | Schael | 210/929 |
| 4,275,726 | 6/1981 | Schael | 210/929 |
| 4,368,739 | 1/1983 | Nelson, Jr. | 604/101 |
| 4,392,855 | 7/1983 | Oreopoulos et al. | 604/29 |
| 4,498,900 | 2/1985 | Buoncristiani | 604/28 |
| 4,637,814 | 1/1987 | Leiboff | 604/28 |
| 4,718,890 | 1/1988 | Peabody | 604/29 |
| 4,911,163 | 3/1990 | Fina | 604/101 |
| 4,942,880 | 7/1990 | Slovák | 128/734 |
| 5,004,459 | 4/1991 | Peabody et al. | 604/29 |
| 5,059,178 | 10/1991 | Ya | 604/96 |
| 5,236,413 | 8/1993 | Feiring | 604/21 |
| 5,256,141 | 10/1993 | Gencheff et al. | 604/53 |
| 5,312,343 | 5/1994 | Krog et al. | 604/101 |

*Primary Examiner*—John Kim
*Attorney, Agent, or Firm*—Robert D. Katz; Peter J. Phillips

[57] ABSTRACT

A dialysis system and method for removing toxic matter from the large intestine comprises an input tube, an output tube concentric with the input tube, both of which tubes are to be inserted in the large intestine an input pressure pump connected to deliver filtrate solution from an input container to the input tube, and an output suction pump connected to the output tube to remove filtrate solution. Pressure gauges control the input and output pumps so that an input pressure level of 75 mm Hg is not exceeded, and so that the output suction pump is disabled unless the input pressure level exceeds 45 mm Hg. A filtrate solution composition comprising a vasodilator of niacin, a high molecular weight protein in the form of casein, a mineral constituents and other components is also provided.

19 Claims, 2 Drawing Sheets

DIALYSIS SYSTEM AND METHOD FOR REMOVING TOXIC MATTER FROM THE SERUM OF THE LARGE INTESTINE

CROSS-REFERENCE TO RELATED APPLICATIONS

This application is a continuation-in-part of U.S. patent application Ser. No. 07/922,673, filed Jul. 30, 1992, now abandoned.

BACKGROUND OF THE INVENTION

The present invention is directed to a dialysis system, method and filtrate solution composition especially useful for removing toxic matter from the serum of the large intestine.

SUMMARY OF THE INVENTION

It is an object of the present invention to replace normal hemodialysis in the filtration of toxic substances in the serum.

It is another object of the present invention to provide a dialysis system and method for a patient which will result in substantially no blood loss during dialysis treatment.

It is yet another objection of the present invention to provide a dialysis system and method which substantially eliminates the risk of infection.

It is a further object of the present invention to provide a dialysis system and method using components which are relatively low in cost so that each patient should be able to afford his or her own individual system, which will further allow for increased time available for dialysis, therefore increasing treatment proficiency, and also reduce or substantially eliminate the risk of cross infection.

It is a yet further object of the present invention to provide a dialysis system and method having components which are of simple design and easy to use, thereby obviating the need for specially trained medical technicians.

In accordance with the present invention, dialysis system for removing toxic matter from the serum of the large intestine is provided, comprising means for introducing a dialysis filtrate solution to the large intestine of a patient at a first location, said filtrate providing a vehicle for removing toxic matter from the serum, of the large intestine; and means for removing waste filtrate from the large intestine at a second location spaced from the first location after the filtrate removes toxic matter from the serum.

According to another aspect of the invention, a dialysis method for removing toxic matter from the serum of the large intestine of a patient is provided, comprising introducing a dialysis filtrate solution to the large intestine of a patient at a first location, said filtrate providing a vehicle for removing toxic matter from the serum of the large intestine and removing waste filtrate from the large intestine at a second location spaced from the first location after the filtrate removes toxic matter from the serum.

The invention also provides a filtrate composition for use in dialysis, comprising a vasodilator, a high molecular weight protein to effect osmotic pressure to achieve diffusion of element across the large intestine membrane into the filtrate, and mineral constituents for maintaining proper serum levels in the large intestine.

DETAILED DESCRIPTION OF THE PREFERRED EMBODIMENT

Figure 1:
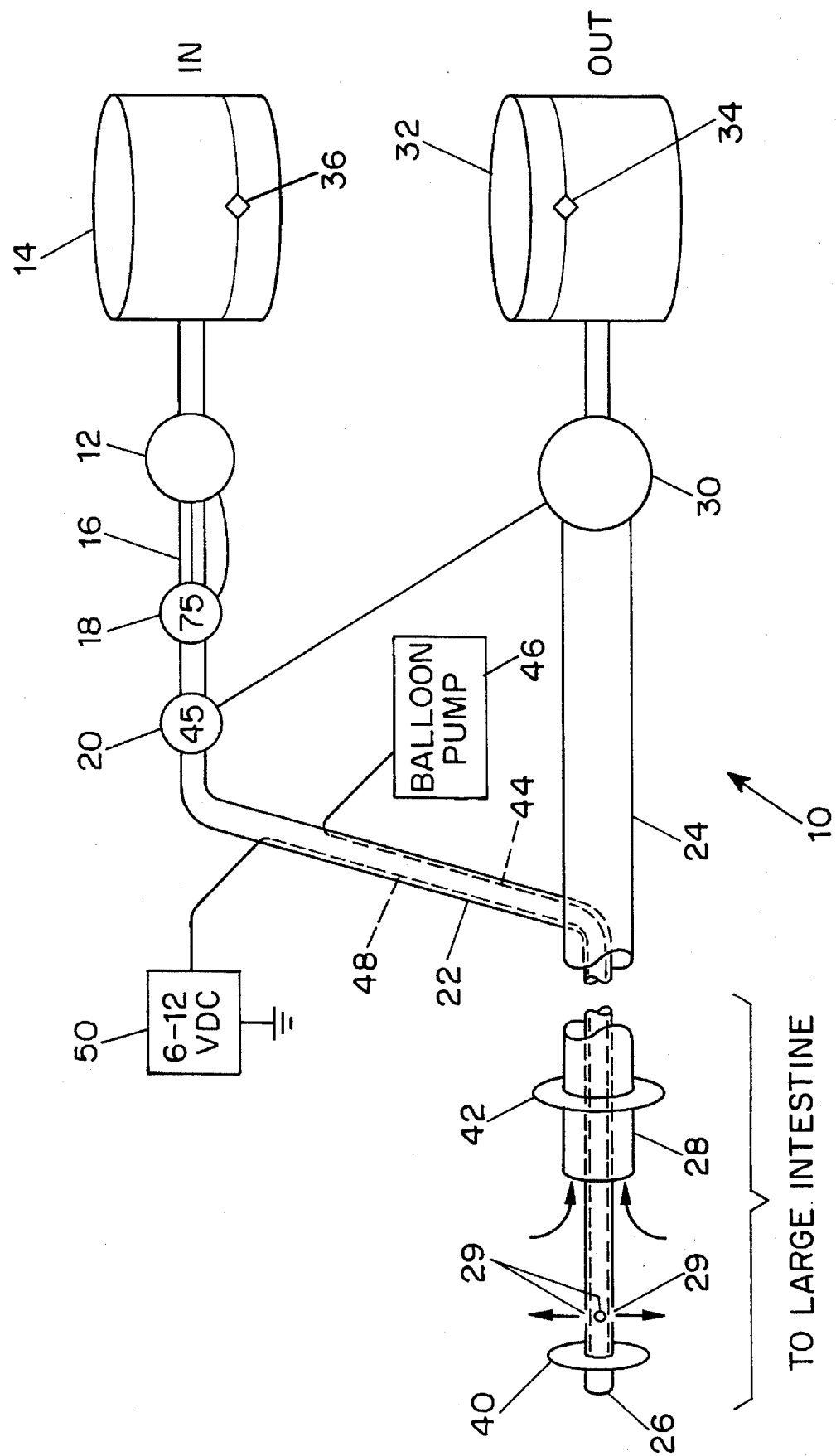
FIG. 1 is a block diagram of a dialysis system according to the present invention.

As shown in FIG. 1, the dialysis system 10 according to the present invention comprises an input pump 12 connected to an input dialysis solution container 14. The input pump 12 has its output 16 connected in line with two pressure gauges, the first one being a 75 mm Hg pressure gauge 18 and the second one being a 45 mm Hg pressure gauge 20. To the output of input pump 12 is connected a flexible plastic input tube 22 which is fed through the sidewall of an output tube 24 also being made of flexible plastic. The input and output tubes 22, 24 are concentric, with the input tube having a distal end 26 about 14–22 inches longer than the distal end 28 of the output tube 24. The differential in the lengths of the two tubes will be determined according to patient size, and of course may be outside of this range. Adjacent the distal end 26 of the input tube are a plurality of openings 29 for introducing the dialysis fluid into the large intestine at a first location. The fluid is removed at a second location as shown by the arrow at the distal end 28 of the output tube 24.

Also shown in the FIG. 1 is an output suction pump 30 connected to an output container 32. The output container 32 has a capacity of about 8 liters and has a float switch 34 to detect when the level of fluid in the output container 32 is greater than about 105% of its capacity, i.e. about 8.4 liters. When the float switch 34 detects that the fluid level exceeds 8.4 liters, the output pump 30 is disabled or de-energized. This action guards against the patient becoming dehydrated. However, if the patient does become dehydrated, he or she may have to drink a small quantity of water or juice to return to normal osmotic balance.

The capacity of the input container 14 is also about 8 liters and also has a float switch 36 disposed close to its bottom. When the level of fluid in the input container 14 is less than a predetermined level of perhaps 1 liter or less, the input pump 12 is disabled.

The 45 mm Hg pressure gauge 20 is connected to the output suction pump 30 so that the output suction pump 30 is enabled or energized when the input pressure is greater than about 45 mm Hg. Of course, the pressure may be different as determined by various clinical trials. The input pump 12 is connected to the 75 mm Hg pressure gauge 18, so that the input pump 12 is disabled when the input pressure exceeds 75 mm Hg. Of course, this value may also be changed depending upon clinical trials.

The pumps 12 and 30 may be operated by AC or DC power. If AC electricity is not available because of power outage or other reasons, a gravity and pressure valve arrangement may be employed.

The length of the concentric tubes is on the order of 36–48 inches. Its outer dimension is about ⅝ inches and its inner dimension is about ⅜ inches. The tubes may be made of flexible plastic to allow for flexibility and ease of cleaning and disinfecting. These may be available as either pre-sterilized and disposable, or reusable after proper sterilization. The ends of the tubes should preferably be rounded and free of sharp angles so as not to perforate the bowel wall of the patient.

In cases where the ileo-cecal has been damaged through disease or surgery, it may be necessary or desirable to incorporate inflatable doughnut-shaped balloons 40, 42 at the end of the tubes, as shown. The balloons are connected to an air line 44 embedded in the input tube, which air line 44 is connected to a balloon pump 46, of conventional design, for inflating and controlling the deflating of the balloons 40, 42.

A wire 48 encased in the input tube may also be provided which carries a low voltage current, for controlling ion flow and increasing osmotic effect of the filtrate solution. The wire 48 is connected to a DC voltage source 50, which is grounded to the patient by a skin electrode, for example.

Figure 2:
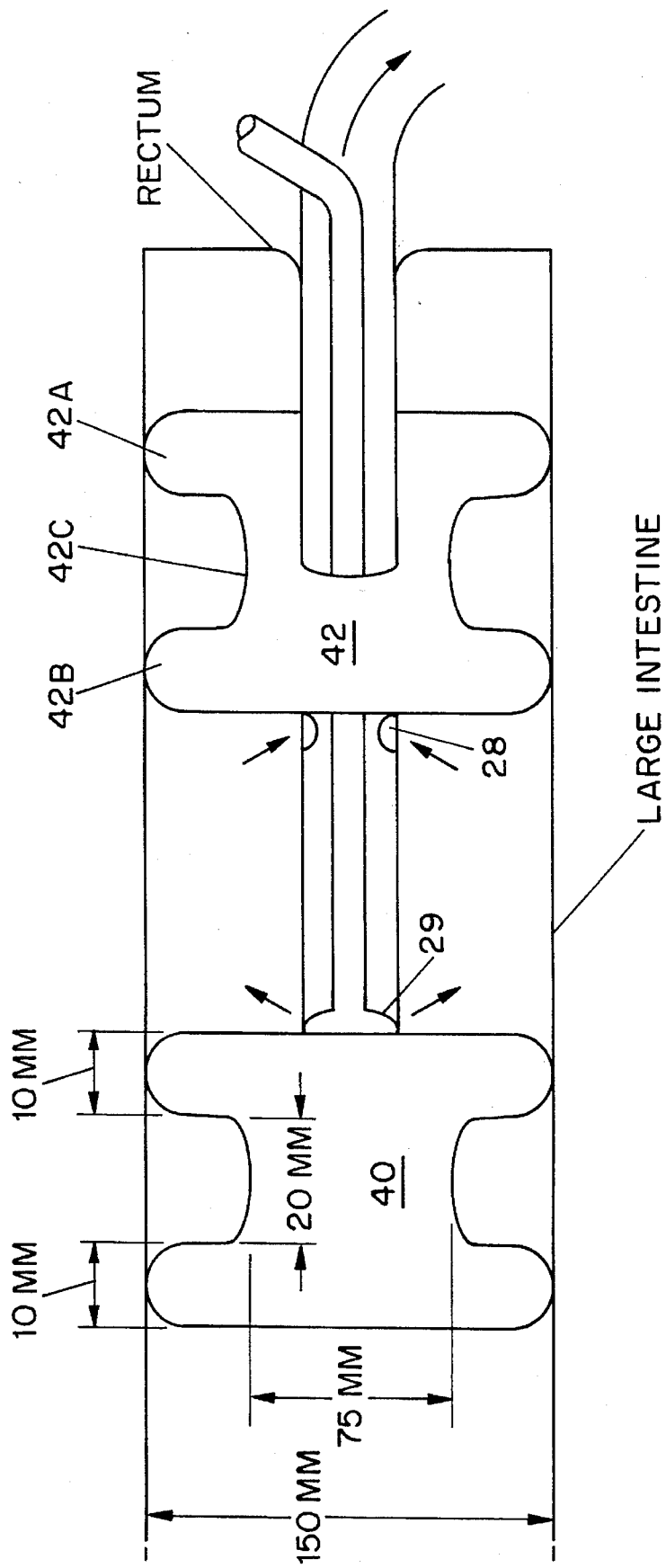
FIG. 2 is an elevational view of a balloon donut design for the dialysis system according to the invention.

FIG. 2 shows a balloon donut design having balloons 40, 42 particularly suited to limit movement from peristalsis, thereby assuring the sealing off of a segment of the large intestine in an area suitable for rapid diffusion. The cellular make-up of the approximately 25 cm of colon proximal to the rectum is stratified, leaving no available diffusible surface area. The balloon 42 is located preferably at least 25 cm from the rectum and is formed of two spaced donut portions 42A and 42B. Each donut portion is inflatable to a 150 mm maximum diameter. The inner or middle portion 42C is inflatable to maximum diameter of 75 mm. The width of the inner portion 42C is about 20 mm, and the width of the outer portions 42A, 42B are each about 10 mm, these dimensions being exemplary and not limiting. Balloon 40 is similarly arranged. Leaving a 20 mm gap (between the portions 42A, 42B) in which the myenteric plexus will not be activated by distention should eliminate/reduce peristalsis and thereby maintain ideal position of the sealed off segment in an area richly supplied with cells with great diffusion capability as well as greatly expanded surface area.

The large intestine is a semi-permeable membrane allowing transport or diffusion or water soluble elements. The purpose of the filtrate solution according to the invention is to provide a vehicle in which undesirable elements or toxins may be removed from the serum of the large intestine without affecting the basic homeostatic mechanisms and important mineral and pH balances. The filtrate composition preferably consists of the following components:

TABLE A

| Sodium Chloride | 120 mEq/liter |
| --- | --- |
| Potassium Gluconate | 5.0 mEq/liter |
| Magnesium Citrate | 2.4 mEq/liter |
| Calcium Lactate | 18 mEq/liter |
| Ferrous Citrate | 220 mg./liter |
| Zinc Citrate | 205 mcg./liter |
| Vitamin C (Ascorbic Acid) | 400 mg./liter |
| Lemon bioflavinoids | 15 mg./liter |
| Rutin | 15 mg./liter |
| Hesperidin | 15 mg./liter |
| Acerola | 15 mg./liter |
| Niacin | 20 mg./liter |

Casein (to achieve a filtrate osmolality of 450 mosm/kg)
Sodium Bicarbonate (min. of 40 mEq/liter) and Glucoronic Acid to produce a highly buffered pH of 7.38 pH.

The mineral constituents serve to maintain proper serum levels of the associated minerals. Niacin is provided for its vasodilator effect and the concomitant effect to increase blood supply to the area, thereby shorting time for serum filtration. Casein is provided to introduce a high molecular weight protein that is not available to transport through the membrane wall, i.e. to effect the osmotic pressure that will achieve diffusion of elements across the membrane into the filtrate. The filtrate is in a water base and is buffered preferably to a pH of 7.38. It should of course be understood that the concentration values given may be adjusted or changed after clinical test. The make up of the components may be modified to adjust to individual, metabolic distortions or to sensitivities to the components of the patient.

Although one preferred embodiment of the system, method and composition according to the present invention have been shown and described, it will be understood that numerous variations and modifications may be effected without departing from the true novel concept and spirit of the present invention. Accordingly, the present invention is not limited to the preferred embodiment disclosed, and is defined by the appended claims.

What is claimed:

1. A dialysis system for removing toxic matter from the serum of the large intestine, comprising:

means for introducing a dialysis filtrate solution to the large intestine of a patient at a first location, said dialysis filtrate solution providing a vehicle for removing toxic matter from the serum of the large intestine, said means for introducing comprising a flexible input tube having a distal end for insertion into the large intestine and having a first inflatable balloon at the distal end of said flexible input tube, said first inflatable balloon having a first inflatable portion spaced from a second inflatable portion by an inner middle portion, said first and second inflatable portions being inflatable to a larger diameter than said inner middle portion of said first inflatable balloon to provide a double seal;

means for providing fluid to said first inflatable balloon, said means for providing fluid being independent from said means for introducing a dialysis filtrate solution; and means for removing waste dialysis filtrate solution from the large intestine at a second location spaced from the first location after the dialysis filtrate solution introduced at said first location by said means for introducing removes toxic matter from the serum, said means for removing comprising a flexible output tube having a distal end for insertion into the large intestine and having a second inflatable balloon at the distal end of said flexible output tube, said second inflatable balloon having a first inflatable portion spaced from a second inflatable portion by an inner middle portion, said first and second inflatable portions being inflatable to a larger diameter than said inner middle portion of said second inflatable balloon; said first and second inflatable balloons being spaced from each other for sealing off a portion of the descending colon of the large intestine.

2. The system according to claim 1, wherein the means for introducing dialysis filtrate solution comprises input pump means for introducing dialysis filtrate solution under pressure.

3. The system according to claim 2, further comprising means for regulating the input pressure of the dialysis filtrate solution.

4. The system according to claim 3, wherein the means for regulating comprises gauge and control means for de-energizing the input pump means in response to the input pressure exceeding a certain pressure level.

5. The system according to claim 1, wherein the means for removing waste dialysis filtrate solution comprises output pump means for removing waste dialysis filtrate solution under suction.

6. The system according to claim 5, wherein the means for removing the waste dialysis filtrate solution comprises gauge and control means for energizing the output pump means in response to pressure at the flexible input tube exceeding a certain pressure level.

7. The system according to claim 5, further comprising an output tank connected to said output pump means, said output tank containing waste dialysis filtrate solution and having a float switch for de-energizing said output pump means in response to the waste dialysis filtrate solution in the output tank exceeding a predetermined level.

8. The system according to claim 1, wherein the means for introducing a dialysis filtrate solution comprises a first flexible input tube, and the means for removing the dialysis filtrate solution comprises a flexible output tube concentric with the flexible input tube, each of said tubes having a distal end for insertion into the large intestine.

9. The system according to claim 8, wherein the respective distal ends of flexible input and output tubes are spaced from each other.

10. The system according to claim 8, wherein the flexible input tube has a smaller diameter than the flexible output tube.

11. A dialysis system for removing toxic matter from the serum of the large intestine, comprising:
    input means for introducing a dialysis filtrate solution to the large intestine of a patient at a first location, said dialysis filtrate solution providing a vehicle for removing toxic matter from the serum of the large intestine, said input means comprising:
        an input pump having a pump input port and an output port,
        a flexible input tube having one end connected to the output port of the input pump and having a distal end for insertion into the large intestine, and
        a first inflatable balloon at the distal end of said flexible input tube, said first inflatable balloon having a first inflatable portion spaced from a second inflatable portion by an inner middle portion, said first and second inflatable portions being inflatable to a larger diameter than said inner middle portion of said first inflatable balloon to provide a double seal;
    means for removing waste dialysis filtrate solution from the large intestine at a second location spaced from the first location after the dialysis filtrate solution introduced at said first location by said input means for introducing removes toxic matter from the serum, said means for removing comprising:
        a flexible output tube having a distal end for insertion into the large intestine;
        a second inflatable balloon at the distal end of said flexible output tube, said second inflatable balloon having a first inflatable portion spaced from a second inflatable portion by an inner middle portion, said first and second inflatable portions being inflatable to a larger diameter than said inner middle portion of said second inflatable balloon; and
    an input tank connected to said input pump, said input tank containing dialysis filtrate solution and having a float switch for de-energizing said input pump in response to the quantity of dialysis filtrate solution in the input tank falling below a predetermined level.

12. A dialysis system for removing toxic matter from the serum of the large intestine, comprising:
    means for introducing a dialysis filtrate solution to the large intestine of a patient at a first location, said filtrate providing a vehicle for removing toxic matter from the serum of the large intestine, said means for introducing comprising a flexible input tube having a distal end for insertion into the large intestine and having a first inflatable balloon at the distal end of said flexible input tube, said first inflatable balloon having a first inflatable portion spaced from a second inflatable portion by an inner middle portion, said first and second inflatable portions being inflatable to a larger diameter than said inner middle portion of said first inflatable balloon;
    means for removing waste filtrate from the large intestine at a second location spaced from the first location after the dialysis filtrate solution removes toxic matter from the serum, said means for removing comprising a flexible output tube having a distal end for insertion into the large intestine and having a second inflatable balloon at the distal end of said flexible output tube said second inflatable balloon having a first inflatable portion spaced from a second inflatable portion by an inner middle portion, said first and second inflatable portions being inflatable to a larger diameter than said inner middle portion of said second inflatable balloon; and
    means for creating a DC voltage field in the large intestine for controlling ion flow and increasing osmotic effect of the filtrate solution.

13. A dialysis method for removing toxic matter from the serum of the large intestine of a patient, comprising the steps of:
    introducing into the large intestine of a patient a flexible input tube having a distal end with first and second inflatable balloons spaced from each other at the distal end thereof, wherein each of the first and second inflatable balloons have a first inflatable portion spaced from a second inflatable portion by an inner middle portion, said first and second inflatable portions being inflatable to a larger diameter then said inner middle portion;
    inflating the first and second inflatable balloons to seal off a portion of the large intestine of the patient;
    introducing a dialysis filtrate solution to the large intestine of the patient at a first location adjacent the first inflatable balloon independently after said inflating step, said dialysis filtrate solution providing a vehicle for removing toxic matter from the serum of the large intestine; and
    removing waste filtrate from the large intestine at a second location spaced from the first location adjacent the second inflatable balloon to remove toxic matter from the serum between the first location and second location.

14. The method according to claim 13, wherein the step of introducing a dialysis filtrate solution comprises introducing dialysis filtrate solution under pressure.

15. The method according to claim 14, further comprising the step of regulating the input pressure of the dialysis filtrate solution.

16. The method according to claim 15, wherein the step of regulating comprises maintaining the input pressure of the dialysis filtrate solution at the flexible input tube below a certain pressure level.

17. The method according to claim 13, wherein the step of removing waste filtrate comprises removing waste filtrate under suction.

18. The method according to claim 13, further comprising the step of removing waste filtrate under suction in response to pressure of the dialysis filtrate solution at the flexible input tube exceeding a certain pressure level.

19. A dialysis method for removing toxic matter from the serum of the large intestine of a patient, comprising the steps of:

introducing a dialysis filtrate solution to the large intestine of a patient at a first location, said dialysis filtrate solution providing a vehicle for removing toxic matter from the serum of the large intestine, said step of introducing comprising introducing a flexible input tube having a distal end with a first inflatable balloon into the large intestine wherein said first inflatable balloon has a first inflatable portion spaced from a second inflatable portion by an inner middle portion, said first and second inflatable portions being inflatable to a larger diameter than said inner middle portion of said first inflatable balloon to provide a double seal;

creating a DC voltage field in the large intestine, for controlling ion flow and increasing osmotic effect of the dialysis filtrate solution; and removing waste dialysis filtrate solution from the large intestine at a second location spaced from the first location after the dialysis filtrate solution removes toxic matter from the serum, said step of removing comprising introducing a flexible output tube having a distal end with a second inflatable balloon into the large intestine, wherein said second inflatable balloon has a first inflatable portion spaced from a second inflatable portion by an inner middle portion, said first and second inflatable portions being inflatable to a larger diameter than said inner middle portion of said second inflatable balloon to provide a double seal.

\* \* \* \* \*